United States Patent

Kricka et al.

Patent Number: 4,729,950
Date of Patent: Mar. 8, 1988

[54] ENHANCED LUMINESCENT OR LUMINOMETRIC ASSAY

[75] Inventors: Larry J. Kricka, Birmingham; Angela M. O'Toole, Wolverhampton; Gary H. G. H. Thorpe, Birmingham; Thomas P. Whitehead, Leamington Spa, all of England

[73] Assignee: National Research Development Corporation, London, England

[21] Appl. No.: 760,036

[22] Filed: Jul. 29, 1985

[30] Foreign Application Priority Data

Aug. 7, 1984 [GB] United Kingdom ............... 8420053

[51] Int. Cl.$^4$ .................. C12Q 1/28; G01N 53/00; G01N 21/52
[52] U.S. Cl. ................................ 435/28; 435/7; 435/810; 422/52; 436/800
[58] Field of Search .................. 435/8, 28, 7, 810; 422/52; 436/800; 544/234, 237

[56] References Cited

U.S. PATENT DOCUMENTS

4,290,773 9/1981 Magers et al. .................. 435/28
4,598,044 8/1986 Kricka et al. .................. 435/8

Primary Examiner—Esther M. Kepplinger
Assistant Examiner—William J. Herald
Attorney, Agent, or Firm—Murray and Whisenhunt

[57] ABSTRACT

It has been a problem that the chemiluminescent emission produced by the peroxidase-catalyzed oxidation of a 2,3-dihydro-1,4-phthalazinedione is often weak or gives a poor signal-background ratio and therefore does not give the high degree of sensitivity required for assay purposes, particularly for assay of peroxidase used to label a reagent for example in ELISA. The present invention solves the problem by the finding the certain narrowly defined aromatic amines are enhancers of the reaction and accordingly provides for their use in an assay and kit. The amines are of general formula (I)

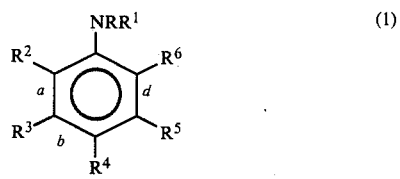

wherein the R symbols (that is, R, $R^1$, $R^2$, $R^3$, $R^4$, $R^5$ and $R^6$) have any of the meanings (a) to (j) given below, all other R symbols in each meaning are hydrogen atoms and the fused rings are to be read in the same configurational sense as formula I:
(a) R=$R^1$=CH$_3$; $R^4$=

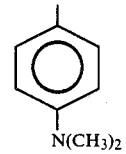

(b) $R^4$=

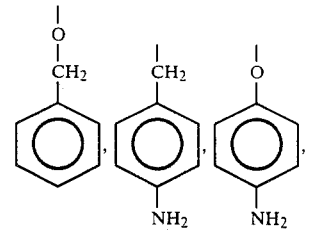

cyclohexyl, or alkyl or alkoxy having 1 to 4 carbon atoms
(c) $R^2$, $R^3$ and $R^4$ together represent the polycyclic fused ring system:

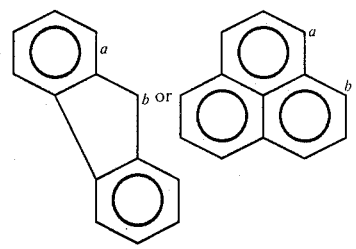

(d) $R^3$ and $R^4$ together represent the fused ring or ring system

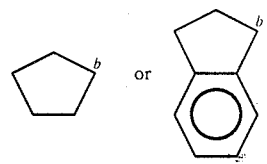

(e) $R^3$ and $R^4$ together represent the fused ring system

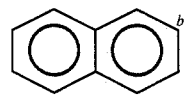

and $R^5$ and $R^6$ together represent the fused ring (Abstract continued on next page.)

(f) $R^2=NH_2$ and $R^4=$
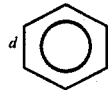
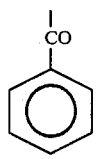
(g) $R^2=R^6=CH_3$ and $R^4=$
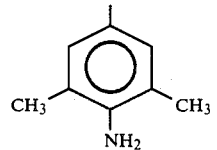
(h) $R^3=C_2H_5$
(i) $R^2=R^4=CH_3$ and
(j) $R^3=R^4=CH_3$.
10 Claims, No Drawings

ENHANCED LUMINESCENT OR LUMINOMETRIC ASSAY

BACKGROUND OF THE INVENTION

1. Field of the Invention

The present invention relates to an enhanced luminescent or luminometric assay, particularly immunoassay, and to a diagnostic kit for use in the assay. The luminescent and luminometric assays with which the present invention is concerned are those depending on a chemiluminescent reaction (a chemical reaction that results in the emission of light). The luminescent emission is generally of sufficient duration to enable the light emitted to be detected or measured, and thereby to allow the detection or quantification of an analyte. The chemiluminescent reaction with which this invention is concerned is that between a 2,3-dihydro-1,4-phthalazinedione (DPD), especially luminol or isoluminol, with an oxidant, especially hydrogen peroxide, and a peroxidase enzyme which catalyses the oxidation of the DPD by the oxidant. The oxidation is accompanied by emission of light.

2. Description of the Prior Art

Luminescent and luminometric assays making use of the above-mentioned peroxidase-catalysed oxidation of a DPD include three major types.

a. Assays wherein a chemiluminescent compound is used directly to label ligands such as proteins, hormones, haptens, steroids, nucleic acids, metabolites, antigens and/or antibodies. The chemiluminescent DPD such as luminol or isoluminol is normally conjugated to a ligand. Chemiluminescence can be detected by adding peroxidase and an oxidant to the reacted conjugate. See for example UK Patent Specifications 2026690A (Miles Laboratories, Inc.), especially page 7 and 2008247A (The Welsh National School of Medicine), especially page 8, Example 7.

b. Assays wherein catalysts or cofactors of luminescent reactions are used as labels, and the luminescent reaction is used to detect or quantitate the label. Normally an enzyme, frequently horseradish peroxidase is conjugated to a ligand. This category therefore includes peroxidase ELISAs.

c. Assays wherein luminescent reactions are used to determine the products formed by the action of enzyme labels other than peroxidase on suitable substrates. An example of this type of assay is the determination of antibody-linked glucose oxidase by reacting the enzyme/antibody reagent with glucose to form hydrogen peroxide and then measuring the amount of hydrogen peroxide produced by adding luminol and a peroxidase catalyst under controlled conditions to initiate a luminescent reaction.

Examples of assays which are not immunoassays but which make use of a luminescent reaction include:

a. An elastase assay based on the release of peroxidase from an insoluble peroxidase-elastin preparation, b. A glucose assay based on co-immobilised glucose oxidase and peroxidase, and c. An assay of a peroxidase enzyme, a 2,3-dihydro-1,4-phthalazinedione, or an oxidant, such as hydrogen peroxide, when these materials are neither labels nor the products of labels.

A review of luminescent and luminometric assays is given by T P Whitehead et al., Clinical Chemistry 25 1531–1546 (1979).

The sensitivity of immunoassays is determined in part by the lower limit for detection of the label or the product of the label. In the case of luminescent or luminometric immunoassays their sensitivity will depend partially on the light emitted in the luminescent reaction per unit of labelled material.

Peroxidases catalyse the oxidation of a wide variety of organic compounds. Advantage has been taken of these reactions for assay purposes by measuring colour formed, fluorescence (=photoluminescence, caused by the action of light on the reaction product) or chemiluminescence (caused by release of light by the reaction carried out in the dark).

Many different colour-forming substrates are mentioned in a review of prior art in Research Disclosure No 16034, anonymous, 19–24 (August 1977). They include aromatic monoamines, eg aniline and its derivatives, diamines such as o- and p-phenylenediamine and benzidine, monophenols, polyphenols, aromatic acids, leuco dyes, coloured dyes such as 2,6-dichlorophenolindophenol, various biological substances, gums, various iodides, bilirubin and the dyes 2,2'-azino-di-(3-ethylbenzthiazoline)-6-sulphonate (ABTS) and 3,3'-diaminobenzidine. The Research Disclosure paper also describes other colour-formers, viz. (1) a sulphonyl hydrazone containing an N-heterocyclic ring in combination with a coupler, eg a phenol or aromatic amine, and (2) a triarylimidazole. Other colour-forming substrates have been summarised by D J Capaldi et al., Analytical Biochemistry 129 329–336 (1983). These authors refer to the redox substrates ABTS and o-dianisidine (3,3'-dimethoxybenzidine) and to colour-forming combinations of compounds including 4-aminoantipyrine with a phenol, 3-methyl-2-benzothiazolinone hydrazone (MBTH) together with N,N-dimethylaniline, 2-hydroxy-3,5-dichlorobenzene sulphonate or 3-(N,N-dimethylamino)benzoic acid.

The use of 4-aminoantipyrine with a phenol coupler is described by C. C. Allain et al., Clinical Chemistry 20, 470 to 475 (1974) and with N,N-dimethylaniline as a coupler by T Kikuchi et al., Chemical Abstracts 94, 1799v (1981) and Y Tsutomu, Chemical Abstracts 94 79759b (1981). See also M Tsuda, Chemical Abstracts 93, 65423e (1980) and Eikenchemical Ltd, 94 135589k (1981). P Josephy et al., J Biol. Chem. 257, 3669–3675 (1982) describes a study of the HRP-catalysed oxidation of the colour-forming compound 3,5,3',5'-tetramethylbenzidine.

Compounds which on oxidation by $H_2O_2$ and peroxidase give fluorescent products include tyramine (4-hydroxyphenethylamine) and homovanillic acid: K Matsuoka et al., Chem. Pharm. Bull. 27, 2345–2350 (1979), 4-hydroxyphenylacetic acid: S D Lidofsky et al., Proc. Nat. Acad. Sci. USA 78, 1901–1905 (1980), various phenols: K Zaitsu et al., Analytical Biochemistry 109, 109–113 (1980) and the amino acid tyrosine: J Williams et al., Biochem. J. 121, 203–209 (1971).

Luminescent substrates other than DPDs include polyphenols such as pyrogallol, lophine which is 2,4,5-triphenylimidazole, acridinium compounds and diaryl oxalates, see the review by T P Whitehead et al. supra.

Enhancement of peroxidase-catalysed oxidations of various organic compounds by various enhancers (which increase reaction rate or intensity of the colour or luminescence measured) has been reported as shown in the following Tables 1 and 2.

TABLE 1

Enhancement of non-luminescent reactions involving a peroxidase

| Reactants | Enhancer | Reference |
| --- | --- | --- |
| o-Methoxyphenol/$H_2O_2$/HRP (Guaiacol) | KCl, NaCl, LiCl or sodium sulphate | A |
| 3,3'-Dimethoxybenzidine/$H_2O_2$/HRP p-Phenylenediamine/$H_2O_2$/HRP | Ammonia and ammonium salts, pyridine and imidazole | B |
| Diaminobenzidine/$H_2O_2$/HRP | Imidazole | C |
| ABTS and other colour-forming and fluorescent substrates | Various phenols | D |
| Ascorbic acid/$H_2O_2$/HRP | o-Methoxy phenol, p-Hydroxydiphenyl or p-Methoxy phenol | E |
| " | p-Cresol | F |
| " | 1,3-Dihydroxybenzene | G |
| " | Thyroxine and Thyroxine analogues | H |
| Epinephrine/$H_2O_2$/HRP | Thyroxine and thyroxine analogues | H |
| Ferrocyanide/$H_2O_2$/HRP | Benzohydroxamic acid | J |
| 1-Anilino-8-naphthalene sulphonate/$H_2O_2$/HRP 2-p-Toluidinyl naphthylene-6-sulphonate/$H_2O_2$/HRP | Benzohydroxamic acid | K |
| Indole-3-acetic acid/$H_2O_2$/HRP | 2,4-Dichlorophenol | L |

TABLE 2

Enhancement of luminescent reactions involving a peroxidase

| Reactants | Enhancer | Reference |
| --- | --- | --- |
| Purpurogallin/$H_2O_2$ | Para-phenylenediamine | M |
| Pyrogallol/$H_2O_2$ | Ortho-phenylenediamine | N |

REFERENCES FOR TABLES 1 AND 2

A: J. R. Whitaker et al., Biochim. Biophys. Acta 62, 310–317 (1962)

B: I. Fridovich, J. Biol. Chem. 238, 3921–3927 (1963)

C: W. Straus, Journal of Histochem. Cytochem. 30, 491–493 (1982)

D: U.S. Pat. No. 4,521,511 (Enzyme Technology Company) issued June 4, 1985.

E: B. Chance, Arch. Biochem. Biophys. 41, 389–410 (1952)

F: I. Yamazaki, "Free Radicals in Biology" Vol III, Ed. W. A. Pryor, Academic Press, New York 1977, Chapter 5, pages 183–218

G: I. Yamazaki, et al., Biochim. Biophys. Acta 77, 47–64 (1963).

H: S. J. Klebanoff, J Biol. Chem. 234, 2437–2442 (1979)

J: I. Aviram, Arch. Biochem. Biophys. 212, 483–496 (1981)

K: L. Sasson et al., Arch. Biochem Biophys. 217, 529–535 (1982)

L: L. R. Fox et al., Plant Physiology 43, 454–456 (1968)

M: M. Halmann et al., Photochemistry and Photobiology 30, 165–167 (1979)

N: G. Ahnstrom et al., Acta. Chem. Scand 19, 313–316 (1965)

It has previously been found that the sensitivity of the peroxidase-catalysed chemiluminescent oxidation of DPDs can be enhanced by including in the reagents an enhancer, namely a 6-hydroxybenzothiazole (European Patent Specification 87959A published Sept. 7, 1983 and subsequently assigned to National Research Development Corporation) and certain phenols (European Patent Specification 116454A published Aug. 22, 1984 and subsequently assigned to National Research Development Corporation).

Whether the peroxidase-catalysed oxidation of a DPD will be enhanced by a given compound is not predictable. For example, no significant enhancement has been obtained with phenol itself and there is a suggestion in the prior art that it is an inhibitor. See "Heterocyclic Compounds" ed. R C Elderfield, John Wiley & Sons, Inc., Volume 6, Chapter 6, pages 228–230, at page 230 middle. Whereas 4-halophenols are good enhancers, 4-aminophenol, 4-cyanophenol and 4-methoxyphenol are not. Many other examples can be given.

SUMMARY OF THE INVENTION

The present invention is based upon the finding that certain aromatic amines significantly enhance the sensitivity of the luminescent reaction of the peroxidase-catalysed oxidation of the 2,3-dihydro-1,4-phthalazinedione (DPD).

In the present specification the term "enhanced" means that the total light emission of the present luminescent reaction and/or the signal/background ratio of the present luminescent reaction is greater than that achieved by the 2,3-dihydro-1,4-phthalazinedione/oxidant/peroxidase system in the absence of sensitivity enhancer.

According to the present invention there is provided an assay which comprises carrying out a chemiluminescent reaction between a peroxidase enzyme, an oxidant, and a chemiluminescent 2,3-dihydro-1,4-phthalazinedione and measuring or detecting the chemiluminescence thereby produced, characterised in that the reaction is carried out in the presence of an aromatic amine of the general formula

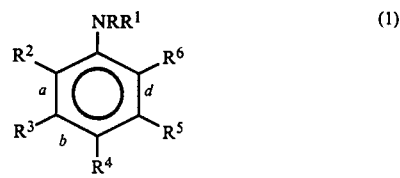
(1)

wherein the R symbols (that is, R, $R^1$, $R^2$, $R^3$, $R^4$, $R^5$ and $R^6$) have any of the meanings (a) to (j) given below, all other R symbols in each meaning are hydrogen atoms and the fused rings are to be read in the same configurational sense as formula 1:

(a) R=R¹=CH₃; R⁴=

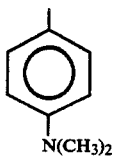

(b) R⁴=

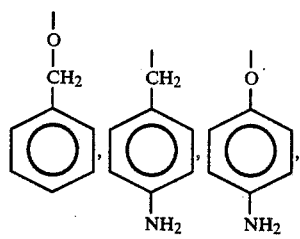

cyclohexyl, or alkyl or alkoxy having 1 to 4 carbon atoms.

(c) R², R³ and R⁴ together represent the polycyclic fused ring system:

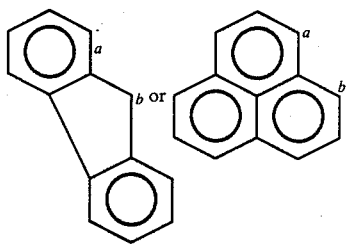

(d) R³ and R⁴ together represent the fused ring or ring system

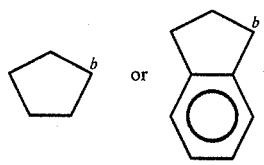

(e) R³ and R⁴ together represent the fused ring system

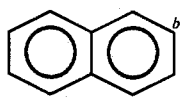

and R⁵ and R⁶ together represent the fused ring

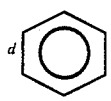

(f) R²=NH₂ and R⁴=

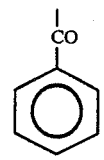

(g) R²=R⁶=CH₃ and R⁴=

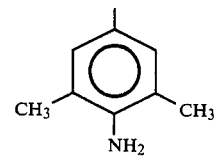

(h) R³=C₂H₅
(i) R²=R⁴=CH₃ and
(j) R³=R⁴=CH₃

The invention also includes a kit for carrying out the assay comprising the DPD, the peroxidase enzyme and the aromatic amine.

DESCRIPTION OF THE PREFERRED EMBODIMENTS

The chemiluminescent 2,3-dihydro-1,4-phthalazinedione (DPD) may be any free or conjugated DPD that is converted to an excited state in a chemiluminescent reaction and then returns to a nonexcited state with the emission of light.

Preferably the 2,3-dihydro-1,4-phthalazinedione is of general formula (2)

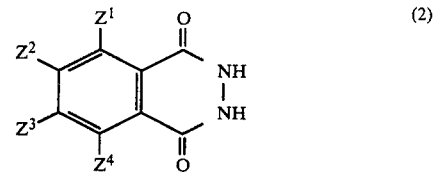

(2)

wherein $Z^1$ is amino or substituted amino, and each of $Z^2$, $Z^3$ and $Z^4$ is H, optionally substituted $C_1$-$C_6$ alkyl, optionally substituted $C_1$-$C_6$ alkenyl, hydroxyl, $C_1$-$C_6$ alkoxyl, carboxyl, amino or substituted amino, or $Z^2$ is amino or substituted amino and each of $Z^1$, $Z^3$ and $Z^4$ is H, optionally substituted $C_1$-$C_6$ alkyl, optionally substituted $C_1$-$C_6$ alkenyl, hydroxyl, $C_1$-$C_6$ alkoxy, carboxyl, amino or substituted amino, or $Z^1$ and $Z^2$ are taken together and are an amino or substituted amino derivative of a benzo group and each of $Z^3$ and $Z^4$ is H, optionally substituted $C_1$-$C_6$ alkyl, optionally substituted $C_{1-6}$ alkenyl, hydroxyl, $C_1$-$C_6$ alkoxyl, amino or substituted amino (In the present specification the term "substituted amino" includes for example alkylcarbonyl-substituted amino, i.e. amido, and aminoalkyl and amidoalkyl substituted amino.) Particularly preferred DPDs for use in the present assay are luminol and isoluminol.

The form which the chemiluminescent DPD takes in the luminescent reaction of the present invention will depend upon the type of assay under consideration. In the case of assays, such as organoluminescent or organoluminometric immunoassays, in which the phthalazinedione is used as a label the chemiluminescent DPD will be a substituted amino derivative of a 2,3-dihydro-1,4-phthalazinedione wherein the amino group is coupled to a ligand such as a protein, hormone, hapten, steroid, nucleic acid, metabolite, antigen or antibody. The amino group may be coupled directly to the ligand or via a bridging arm. Suitable bridging arms will be well known to those skilled in this art, as is evidenced by the discussion thereof in UK Specification 2008247A and U.S. Pat. No. 4,104,029. Preferred bridging arms include those derived from hemisuccinate, hemiglutarate, hemimaleate, carboxymethyl, glucuronide, mercaptoacetate and carboxymethyl derivatives. The amino group may be coupled to the ligand by any suitable well known procedure. Again, certain of these procedures are discussed in UK Specification 2008247A and U.S. Pat. No. 4,104,029. Preferred coupling procedures include the use of mixed anhydrides, carbodiimides and/or active esters.

Although chemiluminescent DPDs suitable for use in those assays which employ a phthalazinedione as a label may be any substituted amino derivative of a 2,3-dihydro-1,4-phthalazinedione with the amino group coupled to a ligand, the preferred substances are 5-amino-2,3-dihydro-1,4-phthalazinedione (luminol) and 6-amino-2,3-dihydro-1,4-phthalazinedione (isoluminol), in each case with the amino group coupled to a ligand, especially to an antibody.

In the case of assays other than those using phthalazinediones as labels the chemiluminescent DPD will ordinarily be free in solution or immobilised on a matrix. Particularly preferred DPDs are again luminol and isoluminol.

Any of the above-defined aromatic amines may be used in the present assay.

The inventors have found, however, that numerous other aromatic amines not within the definition do not give a significant or useful degree enhancement of the peroxidase-catalysed DPD oxidation. Examples of such non-enhancers or feeble enhancers include aniline itself, 4-haloanilines (halogen atom=Cl, Br, I), 4-decylaniline, 2,4-dichloroaniline, 2-chloro-4-methylaniline, 3-haloanilines (halogen atom=Cl, Br, I), 3-methoxyaniline, N,N-dimethylaniline and N-ethylaniline, 1-aminoanthracene, and pyridine. 4-Aminoaniline (p-phenylenediamine) is actually an inhibitor (These results were obtained as follows. A solution of the enhancer (1 mg/ml) in DMSO was prepared. Various amounts of this solution (5, 10 or 20 $\mu$l) were added to 950 $\mu$l of a mixture of sodium luminol (25 mg) in Tris buffer (0.1 mol/l, pH 8.5), (100 ml) containing hydrogen peroxide (30% w/v) (31 $\mu$l) and 10 $\mu$l of a 1 in 1000 dilution of antibody conjugated to horseradish peroxidase. The light emission, at each concentration of enhancer, was recorded using a luminometer built at the Wolfson Research Laboratories. For each enhancer the light emission was also recorded for a blank (blank 1) in which the peroxidase conjugate was omitted and a blank (blank 2) in which the peroxidase conjugate and the enhancer were omitted.)

It will be apparent, therefore, that the invention was made against the background of a very considerable element of unpredictability and it is for this reason that the definition of the enhancers herein is closely allied to the experimental results presented in Table 3 in the Examples.

The preferred aromatic amine enhancers are N,N,N',N'-tetramethylbenzidine, 4-benzyloxyaniline, 4-methoxyaniline and 3-aminofluoranthrene.

In general any peroxidase enzyme (EC No. 1.11.1.7) which catalyses the luminescent reaction of a 2,3-dihydro-1,4-phthalazinedione, especially luminol, may be used in the luminescent reaction of the present invention. Examples include the plant peroxidases. Preferably the enzyme is horseradish peroxidase. Any ordinary horseradish peroxidase (HRP), produced without any unusual purification procedure, is suitable for use in the invention. For example the HRP used for normal assay purposes, eg normally used to label antibodies for ELISA, are suitable. However, the inventors' experiences indicate that acidic peroxidase isoenzymes such as Sigma Types VII and VIII might not give significant enhancement. These esoteric materials are many times the price of Sigma Type VI which is one of the ordinary HRPs useful in this invention.

The term "peroxidase" as used herein does not extend to microperoxidase, haemoglobin, haematin and myoglobin.

The form which the peroxidase enzyme takes in the luminescent reaction of the present invention will depend upon the type of assay under consideration. In the case of assays, especially immunoassays, wherein the peroxidase is used as a label it will be coupled (conjugated) to a ligand such as a protein, hormone, hapten, steroid, nucleic acid, metabolite, antigen or antibody. Generally the peroxidase will be coupled to the ligand via a bridging arm. Suitable bridging arms and coupling procedures are any of those well known.

In the case of assays other than those using peroxidase as a label, the enzyme will be in its free form, either in solution or immobilised on a matrix, not coupled to a ligand.

Any oxidant which reacts with peroxidase and a DPD, especially luminol or isoluminol, to cause excitation of the DPD so that it emits light in a luminescent reaction, may be used in the present luminescent reaction. Particularly preferred oxidants are hydrogen peroxide and perborate ion.

In assays, especially immunoassays, which employ a 2,3-dihydro-1,4-phthalazinedione, or a peroxidase enzyme as a label for a ligand, a known quantity of the oxidant will be added to the reaction mixture, generally from a proprietary source. In certain other assays however, the amount of oxidant, generally hydrogen peroxide, present will be unknown. In this second type of assay the label will be a substance, often an enzyme such as glucose oxidase, which participates in the conversion of a substrate into the oxidant. Thus, in this case, the present luminescent reaction will be used to determine the quantity of labelled ligand by the measurement of the oxidant concentration in the luminescent reaction mixture.

Light emission from the luminescent reaction of the present invention, although depending primarily on the choice of peroxidase, oxidant, sensitivity enhancer and chemiluminescent DPD, will also be determined by secondary factors such as temperature, pH, reagent concentration, mixing speed and method of light measurement. To maximise the sensitivity of the present system these secondary factors should be adjusted to obtain the maximum light emission, in a reproducible and easily measurable manner, with the signal to background ratio as high as possible.

The conditions chosen are generally a compromise involving the enzyme or catalytic activity of the peroxidase, the kinetics of the reaction, the apparatus employed, the signal to background ratio and the sensitivity required.

The present inventors have found that in order to achieve optimum results the present luminescent reaction should be conducted under moderate conditions of temperature, ranging from 10° to 50° C., and pH, in the range of 6 to 10, most often between 7 and 9. Suitable buffering substances for the method of the present invention are phosphate, tris(hydroxymethyl)aminomethane, 2-amino-2-methyl-1,3-propanediol, acetate, carbonate and borate.

Generally, the concentrations of the reagents in the luminescent reaction mixture, with the exception of the material to be determined, are kept constant. The variable factor may be, for example, the concentration of a labelled ligand, a product of a label, an oxidant or unbound peroxidase.

The following reagent concentrations are particularly suitable for use in the present luminescent reaction:
peroxidase: 0.1 µg–5000 mg/liter
oxidant: 10 µmol–300 mmol/liter
chemiluminescent DPD: 0.5 µmol–200 mmol/liter
aromatic amine enhancer: 0.1 µmol–100 mmol/liter In performing the present luminescent reaction, certain of the four essential reagents (but omitting at least one) are placed in a sample tube. The luminescent reaction is then triggered by the addition, to the tube, of the missing essential reagent(s). The light emitted may be quantified by a standard measuring device, such as a photomultiplier tube, the signal from which is fed to and displayed or recorded on a recorder, oscilliscope or scalar. The light may also in some cases be observed by the naked eye or recorded on a photographic plate. Preferably however the light is quantified on a luminometer of the type described in UK Patent Application No. 2025609A.

The luminescent reaction of the present invention may be used in three major types of immunoassay, the distinguishing feature of each being the type of label attached to the ligand. The labels are:

a. an amino or a substituted amino derivative of a 2,3-dihydro-1,4-phthalazinedione, wherein the amino group is coupled to the ligand.
b. a peroxidase enzyme, and
c. a substance, other than those listed under a and b and generally an enzyme such as glucose oxidase, which participates in the conversion of a substrate to a material which may be determined by the present luminescent reaction (generally hydrogen peroxide or peroxidase).

In the above immunoassays labelling of the substance to be assayed or of an antibody to such a substance is possible.

Depending on the type of label employed, the assay may be either heterogeneous or homogenous. In the former case complex fluids such as serum may be analysed, however, in the latter case, a preliminary extraction or purification step may be necessary.

Typical heterogeneous and homogenous luminescent or luminometric immunoassays are outlined below:

1. Heterogeneous Luminescent or Luminometric Immunoassay

In this type of immunoassay the substance to be assayed is reacted with an antibody thereto. The free antibody is then separated from the bound antibody. The reaction is quantified by labelling either the antibody, the substance to be assayed or another molecule which can react with the free or bound moieties after separation.

2. Competitive Heterogeneous Luminescent Immunoassay

In this case an unknown amount of the substance to be assayed is mixed with a known amount of said substance coupled with a label and a known, but limited, amount of an antibody thereto. A competitive reaction between the labelled and unlabelled substance for the antibody ensues. The complexes between antibody and unlabelled substance and between antibody and labelled substances are separated from the free labelled and unlabelled substance.

The amount of labelled substance bound to antibody is related to the amount of unlabelled substance in the solution being assayed. These quantities may be determined either by measuring the amount of label bound to antibody or by measuring the amount of free labelled substance remaining. Examples of this type of assay wherein peroxidase is the label and the antibody is bound to a solid phase, viz. the walls of a glass test tube, are given in UK 2044927A.

3. "Two-Site" Heterogeneous Luminometric Immunoassay

In this type of immunoassay the substance to be assayed is first bound to an unlabelled antibody thereto which in turn is bound to a solid phase support, such as plastic. The complex (between antibody and substance) is then treated with a labelled antibody. Analysis for the labelled antibody in the solid complex obtained may then be effected by separating the solid complex from the solution, and then determining either the amount of label present in the separated solid complex or the amount of label present in the residual labelled antibody dissolved in the solution.

4. Homogeneous Luminescent or Luminometric Immunoassay

This is applicable to immunoassays wherein the label is an amino or a substituted amino derivative of a 2,3-dihydro-1,4-phthalazinedione. It depends upon the light emitted from the free labelled substance of interest (or antibody thereto) being of a different intensity or wavelength to the light emitted from the bound labelled substance of interest (or antibody thereto).

In one example it was found that the intensity of light emitted from the reaction of a (progesterone-isoluminol derivative) conjugate, a haem catalyst and hydrogen peroxide was of a lower intensity than the same reaction performed in the presence of anti-progesterone IgG.

Thus in the assay an unknown progesterone sample was first incubated with a known amount of anti-progesterone IgG. After equilibrium was reached by known amount of progesterone-isoluminol derivative conjugate was added, followed by a known amount of haem and hydrogen peroxide. The light emitted was measured and the amount of progesterone present in the unknown sample thereby determined from the standard curve. (The more progesterone present in the unknown sample, the less free IgG is left at equilibrium and the lower is the light yield of the luminescent reaction.)

In this way the determination of progesterone may be achieved without the requirement of a separation step.

In all of the above immunoassays the quantifying, detecting or locating (strictly, locating is a form of detecting) step may be the luminescent reaction of the present invention.

The antibodies employed in the above immunoassays may be purchased commercially or prepared by known immunological techniques. The antibodies may be in the form of a complex mixture of antibodies or they may be one or more monoclonal antibodies. Only a small volume of antibody is generally required and it is maintained at the condition of pH, ionic strength and temperature appropriate for its activity.

Antibodies to the following non-exhaustive list of substances may be usefully employed in immunoassays utilising the present luminescent reaction: proteins such as insulin, alphafetoprotein and ferritin, hormones such as growth hormone, parathyroid hormone, follicle stimulating hormone, luteinising hormone, thyroid stimulating hormone, adrenocorticotrophic hormone, glucagon, prolactin and calcitonin, haptens/steroids such as estradiol, progesterone and cortisol, drugs such as digoxin, antigens such as well surface antigens and carcinoembryonic antigen and antibodies such as mumps virus antibody, human immunoglobulin G (IgG), rabbit IgG, sheep IgG, guinea pig IgG, donkey IgG and human immunoglobulins E and M.

The luminescent reaction of the present invention may also be used in assays other than the immunoassays described above. These include:

1. The assay of elastase based on the release of peroxidase from an insoluble peroxidase elastin preparation In this assay a solid elastin-peroxidase conjugate is incubated with varying amounts of the enzyme elastase. After a predetermined period unreacted conjugate is removed by centrifugation and the supernatant is assayed for unbound peroxidase.

The amount of unbound peroxidase present in the supernatant is related to the elastase activity in the sample tested.

2. The assay of proteinase based on the release of isoluminol from a synthetic peptide substrate In this assay immobilised synthetic peptide substrate, Affigel 10-Ala-Ala-Ala-Phe-isoluminol, is treated with varying quantities of proteinase. After a predetermined period unreacted substrate is removed by centrifugation and the supernatant is assayed for isoluminol. The amount of isoluminol present in the supernatant is related to proteinase activity in the sample tested.

3. The assay of glucose based on co-immobilised glucose oxidase and peroxidase

In this assay glucose oxidase and peroxidase are co-immobilised on a support, eg Sepharose or plastic tubes. To this is added a solution of luminol and sensitivity enhancer. Finally a solution of glucose is added and the light emission recorded. Light emission is directly related to the amount of glucose in solution.

4. Assay for labelled DNA

In the now well known technique of labelling DNA with biotin, the appropriate binding ligand such as avidin or streptavidin can be labelled with peroxidase and the peroxidase assayed by the method of the invention.

Also, the invention is applicable to DNA labelled in other ways with peroxidase, e.g. see PCT Application No. 84/03520 (A. D. B. Malcolm et al.)

The major use of the present assay will be in clinical laboratories or doctors' surgeries. It is usual for such laboratories and/or surgeries to obtain the materials to be used in a given assay procedure in the form of an assay kit. In addition to the DPD, aromatic amine enhancer and peroxidase, the kit may also contain an oxidant, but in many cases this material may either be provided separately or be the substance to be assayed.

Preferably the peroxidase enzyme, the oxidant, the sensitivity enhancer and the chemiluminescent DPD will each be one of those substances mentioned above as preferred for use in the present assay. In one particularly preferred embodiment of the present assay kit at least one of the peroxidase enzyme and the chemiluminescent DPD is conjugated, eg to an antibody to the sustance to be assayed.

Optionally the assay kit may also contain one or more standard solutions each containing a known amount of the substance to be assayed, and/or one or more of the preferred buffer solutions. Conveniently the assay kit may also include a reaction vessel suitable for use in conjunction with the apparatus used for the determination of the light emitted in the course of carrying out the assay. Also a mixing device may be included in the assay kit, for use in ensuring adequate admixture of the reagents.

EXAMPLES

The following Examples illustrate the invention.

MATERIALS AND METHODS

Reagents

A horseradish peroxidase-labelled rabbit anti-human AFP was obtained from Dako Products, Mercia Brocades Ltd., Brocades House, Pyrford Road, West Byfleet, Weybridge, Surrey, UK.

Enzyme immunoassay kits for the assay of carcinoembryonic antigen (CEA) were supplied by Abbott Laboratories Ltd., Diagnostics Division, Basingstoke, UK.

Luminol (5-amino-2,3-dihydro-1,4-phthalazinedione) and isoluminol (6-amino-2,3-dihydro-1,4-phthalazinedione) were obtained from the Sigma Chemical Co., Poole, Dorset, UK. The sodium salt of luminol was prepared as described previously, Ham et al., Anal. Lett, 1979, 12, (535).

7-Dimethylaminonaphthalene-1,2-dicarboxylic acid hydrazide, formula (2) $Z^1$ and $Z^2$ are taken together and are a dimethylamino substituted benzo group, $Z^3=Z^4=H$, was obtained from Boehringer Mannheim.

N-(6-Aminobutyl)-N-ethylisoluminol was obtained from LKB Finland.

All of the aromatic amines were obtained from the Aldrich Chemical Co.

Analytical Equipment

In the case of Examples 1 to 24, chemiluminescent reactions were carried out in 10 mm×10 mm, 4 ml volume plastic disposable cuvettes (W Sarstedt Ltd, Leicester, LE3 1UQ, UK). The light emitted was quantitated via a luminometer described previously (Carter et al., UKPA 2025609A), incorporating a modification allowing several cuvettes to be successively positioned, accurately and reproducibly, in front of the photocathode of the photomultiplier tube.

Results were displayed on a fast potentiometric chart recorder (Type PM 8202; Philips, Eindhoven, Netherlands; full scale deflection time, less than 0.25 sec).

In the case of the carcinoembryonic antigen assay, chemiluminescent reactions were carried out in 55 mm×11 mm clear polystyrene round bottomed tubes supplied by LIP (Equipment and Services) Ltd., Shipley, West Yorkshire. Automatic initiation of luminescent reactions and measurement of light emission were performed using an Auto-Biolumat LB 950 luminometer supplied by Laboratorium Prof Dr Berthold, Wildbad, West Germany. The instrument employed photoncounting and was controlled by a 48K Apple II Computer.

letters in the left-hand column match the compounds to the meanings of R symbols in formula (1) above.

TABLE 3

Improvement of Signal/Background Ratio by Various Aromatic Amines

| Example | Enhancer | Volume of 4.54 mMole/liter solution added (μl) | Improvement in Signal/Background Ratio | Improvement in Signal |
|---|---|---|---|---|
| Comparative | — | — | 1 | 1 |
| (a) 1 | N,N,N',N'—Tetramethylbenzidine | 20 | 467 | 56 |
| (c) 2 | 1-Aminopyrene | 10 | 196 | 4 |
| (b) 3 | 4-Benzyloxyaniline | 10 | 177 | 30 |
| (c) 4 | 3-Aminofluoranthrene | 10 | 100 | 30 |
| (d) 5 | 5-Aminoindane | 20 | 81 | 6 |
| (b) 6 | 4-Methoxyaniline | 10 | 79 | 23 |
| (e) 7 | 6-Aminochrysene | 10 | 55 | 3 |
| (b) 8 | 4-Aminophenyl ether | 10 | 33 | 18 |
| (d) 9 | 2-Aminofluorene | 10 | 22 | 9 |
| (f) 10 | 3,4-Diaminobenzophenone | 5 | 14 | 5 |
| (g) 11 | 3,3',5,5'-Tetramethylbenzidine | 20 | 12 | 2 |
| (b) 12 | 4-Cyclohexylaniline | 10 | 11.5 | 4 |
| (b) 13 | 4,4'-Methylenedianiline | 20 | 4.1 | 2 to 3 |
| (h) 14 | 3-Ethylaniline | 10 | 4.0 | 3 |
| (i) 15 | 2,4-Dimethyaniline | 5 | 3.5 | 4 |
| (b) 16 | 4-Methylaniline | 20 | 3.0 | 2 |
| (j) 17 | 3,4-Dimethylaniline | 5 | 2.9 | >3 |
| (b) 18 | 4-Ethylaniline | 5 | 2.8 | 1.2 |
| (b) 19 | 4-n-Butylaniline | 10 | 2.3 | 2 |
| (b) 20 | 4-Propylaniline | 5 | 2.1 | 1.8 |

EXAMPLE 1

Luminescent Assay of peroxidase using luminol and N,N,N',N'-tetramethylbenzidine Sodium luminol (50 mg) and hydrogen peroxide (62 μl, 30% w/v) were added to 200 ml Tris buffer (0.1 Molar, pH 8.5). This solution was allowed to stand for about 0.5 hr. before use and was protected from light throughout. To 10 μl of rabbit anti AFPHRP 1:1000 dilution) in a cuvette, 0.9 ml of the luminol/$H_2O_2$ reagent was added. The resultant light emission was recorded before addition of 20 μl of N,N,N',N'-tetramethylbenzidine (4.54 mmole/liter in dimethyl sulphoxide to the reaction mixture. The enhanced light output was similarly recorded and the improvement in signal was determined. The above procedure was repeated omitting the rabbit anti-AFP-HRP to determine the effect of N,N,N',N'-tetramethylbenzidine on the background reading. The improvements in signal and in signal/background ratio were measured and are given in Table 3. The improvement in signal is considered to be the more significant parameter.

EXAMPLES 2-20

The procedure of Example 1 was repeated except that N,N,N',N'-tetramethylbenzidine was replaced by other aromatic amines. The improvement in signal/background ratio was measured and is given in Table 3.

COMPARATIVE EXAMPLE

The procedure of Example 1 was repeated except that no sensitivity enhancer was added to the luminescent reaction mixture. Results are given in Table 3. The

EXAMPLE 21

Stock solutions of isoluminol (24 mg) in 100 ml Tris buffer (0.1M, pH 8.5) and hydrogen peroxide (450 microliters, 30% w/v) in 100 ml Tris buffer (0.1M, pH 8.5) were prepared. The following reagents were added to a cuvette, 50 microliters of stock isoluminol reagent, 50 microliters of stock hydrogen peroxide, 10 microliters of rabbit anti-AFP-HRP (1 in 1000 dilution) and 10 microliters of N,N,N',N'-tetramethylbenzidine (TMB) or 4-benzyloxyaniline (4.54 mmole/liter) in dimethyl sulphoxide. The reagents were mixed and the reaction initiated by the addition of 0.9 ml Tris buffer (0.1M, pH 8.5). The subsequent light emission was measured. In a control experiment, the above procedure was repeated except that 10 microliters of DMSO replaced the amine. A considerable improvement in signal of the TMB- or 4-benzyloxyaniline-enhanced reaction over the control was noted.

EXAMPLE 22

The procedure of Example 21 was repeated except that isoluminol was replaced by N-(6-aminobutyl)-N-ethylisoluminol.

EXAMPLE 23

The procedure of Example 21 was repeated except that isoluminol was replaced by 7-dimethylaminonaphthalene-1,2-dicarboxylic acid hydrazide (9-dimethylamino-2,3-dihydrobenzo(f)phthalazine-1,4-dione).

EXAMPLE 24

The procedure of Example 21 was repeated except that hydrogen peroxide was replaced by sodium perborate and isoluminol by luminol.

In each of Examples 22 to 24 enhancement of light emission on addition of TMB or 4-benzyloxyaniline was noted.

EXAMPLE 25

Assay of carcinoembryonic antigen (CEA)

The assays were performed as described in the manufacturer's instructions; standards (200 microliters), prepared in sodium acetate buffer (0.2 mol/liter, pH 5.0, containing 0.01% Thimerosal preservative) were added to wells of a plastic reaction tray. One plastic bead coated with anti-CEA raised in guinea pigs was rinsed in distilled water and added to each well. The tray was gently tapped to remove any bubbles attached to the bead surface, covered and incubated at 45° C. for two hours in a water bath. Samples were then aspirated and each bead was washed with distilled water (5×2 ml). Goat anti-human CEA-HRP conjugate (200 microliters, ca 0.05 µg/ml in Tris buffer containing protein stabiliser and 0.01% Thimerosal) was added to each bead, and then the tray was treated as before and incubated at 45° C. for two hours. After aspirating each solution, the beads were washed with distilled water (5×2 ml), transferred to (55 mm×11 mm) polystyrene tubes and then washed again (2×4 ml). Bound HRP conjugate was then quantified using the assay of the invention with TMB as enhancer.

To each tube was added 0.5 ml Tris buffer (0.05 mol/liter, pH 8.0). The luminescent reaction was then automatically initiated on the Auto-Biolumat luminometer by injecting 0.5 ml of a luminol/hydrogen peroxide/TMB solution. This solution was earlier prepared by adding 1 ml TMB solution (0.5 mg/ml DMSO) to 100 ml of a luminol (2.5 mmol/liter), hydrogen peroxide (5.4 mmol/liter) mixture prepared in Tris buffer (0.05 mol/liter, pH 8.0).

On initiation of the luminescent reaction, the integrated light emission between 0 and 180 seconds (after initiation) was automatically recorded for each bead. Results are given in Table 4.

EXAMPLE 26

The assays of Example 25 were repeated except that the TMB solution had a concentration of 2.5 mg/ml. Results are given in Table 4.

EXAMPLE 27

The assays of Example 25 were repeated except that the TMB solution had a concentration of 5.0 mg/ml. Results are given in Table 4.

EXAMPLE 28

(Comparative)

The assays of Example 25 were repeated without any TMB solution added. Results are given in Table 4.

TABLE 4

CEA Assays. Photon counts given for various CEA concentrations

| Example | CEA concn (ng/ml) | TMB concn (mg/ml) | Photon counts per 180 sec × $10^{-6}$ |
|---|---|---|---|
| 28 | 0 | — | 16.08 |
| | 2.5 | — | 17.83 |
| | 5.0 | — | 25.24 |
| | 10.0 | — | 46.22 |
| | 22.0 | — | 50.53 |
| 25 | 0 | 0.5 | 8.64 |
| | 2.5 | 0.5 | 39.86 |
| | 5.0 | 0.5 | 84.30 |
| | 10.0 | 0.5 | 148.91 |
| | 20.0 | 0.5 | 341.19 |
| 26 | 0 | 2.5 | 4.08 |
| | 2.5 | 2.5 | 40.56 |
| | 5.0 | 2.5 | 60.13 |
| | 10.0 | 2.5 | 149.86 |
| | 20.0 | 2.5 | 289.55 |
| 27 | 0 | 5.0 | 6.53 |
| | 2.5 | 5.0 | 30.02 |
| | 5.0 | 5.0 | 63.25 |
| | 10.0 | 5.0 | 137.30 |
| | 20.0 | 5.0 | 245.56 |

What is claimed is:

1. In a luminescent or luminometric assay which comprises carrying out a chemiluminescent reaction between a peroxidase, an oxidant, and a chemiluminescent 2,3-dihydro-1,4-phthalazinedione and measuring or detecting the chemiluminescence thereby produced, the improvement wherein the reaction is carried out in the presence of an aromatic amine of the general formula

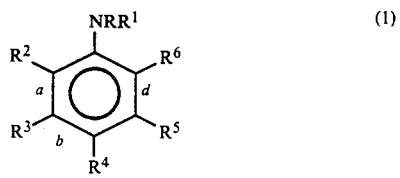

wherein the R symbols, namely R, $R^1$, $R^2$, $R^3$, $R^4$, $R^5$ and $R^6$, have any of the meanings (a) to (j) given below, all other R symbols in each meaning are hydrogen atoms and the fused rings are to be read in the same configurational sense as formula 1, whereby sides "a", "b" and "d" in formula (1) are fused to sides "a", "b" and "d" respectively in the formulae below:

(a) $R=R^1=CH_3$; $R^4=$

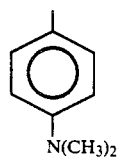

N(CH$_3$)$_2$ (b) $R^4=$

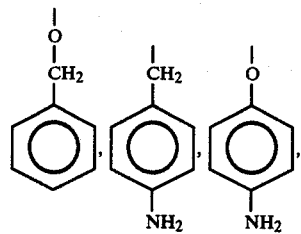

cyclohexyl, or alkyl or alkoxy having 1 to 4 carbon atoms (c) $R^2$, $R^3$ and $R^4$ together represent the polycyclic fused ring system:

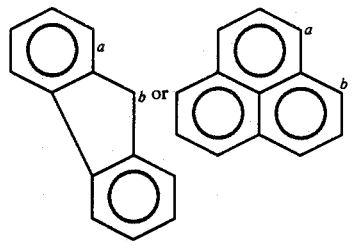

(d) $R^3$ and $R^4$ together represent the fused ring or ring system

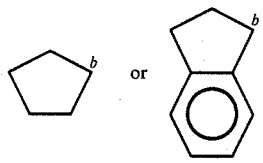

(e) $R^3$ and $R^4$ together represent the fused ring system

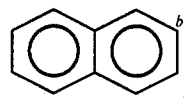

and $R^5$ and $R^6$ together represent the fused ring

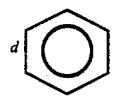

(f) $R^2 = NH_2$ and $R^4 =$

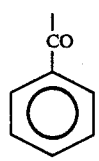

(g) $R^2 = R^6 = CH_3$ and $R^4 =$

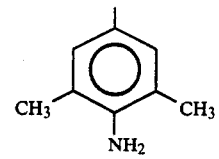

(h) $R^3 = C_2H_5$
(i) $R^2 = R^4 = CH_3$ and
(j) $R^3 = R^4 = CH_3$.

2. An assay according to claim 1 wherein the chemiluminescent 2,3-dihydro-1,4-phthalazinedione is of general formula (2)

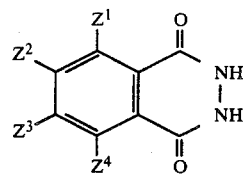

wherein $Z^1$ is amino or substituted amino, and each of $Z^2$, $Z^3$ and $Z^4$ is H, optionally substituted $C_1-C_6$ alkyl, optionally substituted $C_1-C_6$ alkenyl, hydroxyl, $C_1-C_6$ alkoxyl, carboxyl, amino or substituted amino, or $Z^2$ is amino or substituted amino and each of $Z^1$, $Z^3$ and $Z^4$ is H, optionally substituted $C_1-C_6$ alkyl, optionally substituted $C_1-C_6$ alkenyl, hydroxyl, $C_1-C_6$ alkoxyl, carboxyl, amino or substituted amino, or $Z^1$ and $Z^2$ are taken together and are an amino or substituted amino derivative of a benzo group and each of $Z^3$ and $Z^4$ is H, optionally substituted $C_1-C_6$ alkyl, optionally substituted $C_1-C_6$ alkenyl, hydroxyl, $C_1-C_6$ alkoxyl, carboxyl, amino or substituted amino.

3. An assay according to claim 2 wherein the chemiluminescent 2,3-dihydro-1,4-phthalazinedione is luminol or isoluminol.

4. An assay according to claim 1, wherein the peroxidase is horseradish peroxidase.

5. An assay according to claim 1, wherein the peroxidase is present in an analyte in a free or conjugated form and its presence or the amount thereof is deduced from the detection or measurement, respectively, of the chemiluminescence.

6. An assay according to claim 1 wherein the aromatic amine is N,N,N',N'-tetramethylbenzidine, 4-benzyloxyaniline, 3-aminofluoranthrene or 4-methoxyaniline.

7. A kit for use in a luminescent or luminometric assay comprising the following components in separate containers:
 a chemiluminescent 2,3-dihydro-1,4-phthalazinedione,
 a peroxidase, and
 an aromatic amine of the general formula

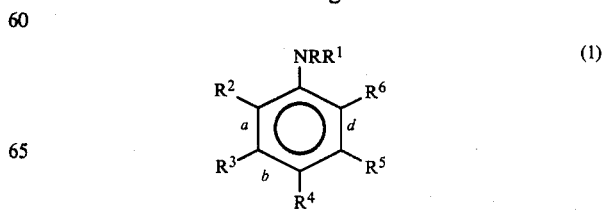

wherein the R symbols, namely R, $R^1$, $R^2$, $R^3$, $R^4$, $R^5$ and $R^6$, have any of the meanings (a) to (j) given below, all other R symbols in each meaning are hydrogen atoms and the fused rings are to be read in the same configurational sense as formula 1, whereby sides "a", "b" and "d" in formula 1 are fused to sides "a", "b" and "d" respectively in the formulae below:

(a) $R=R^1=CH_3$; $R^4=$

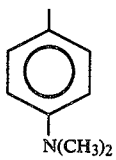

(b) $R^4=$

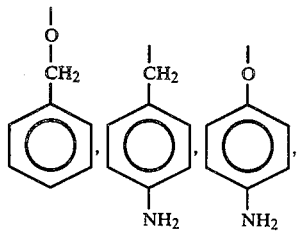

cyclohexyl, or alkyl or alkoxy having 1 to 4 carbon atoms (c) $R^2$, $R^3$ and $R^4$ together represent the polycyclic fused ring system:

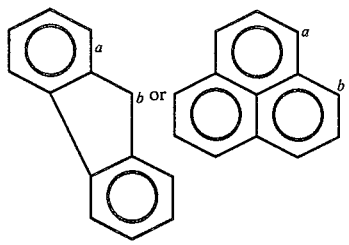

(d) $R^3$ and $R^4$ together represent the fused ring or ring system

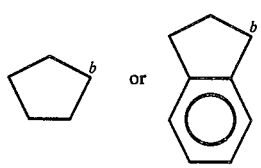

(e) $R^3$ and $R^4$ together represent the fused ring system

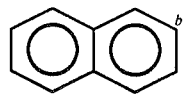

and $R^5$ and $R^6$ together represent the fused ring

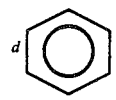

(f) $R^2=NH_2$ and $R^4=$

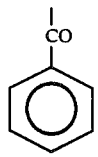

(g) $R^2=R^6=CH_3$ and $R^4=$

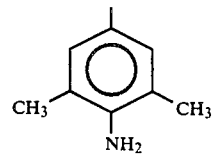

(h) $R^3=C_2H_5$
(i) $R^2=R^4=CH_3$ and
(j) $R^3=R^4=CH_3$.

8. A kit according to claim 7 wherein the chemiluminescent 2,3-dihydro-1,4-phthalazinedione is of general formula (2):

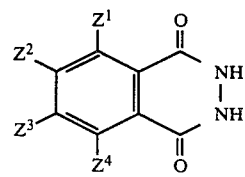
(2)

wherein $Z^1$ is amino or substituted amino, and each of $Z^2$, $Z^3$ and $Z^4$ is H, optionally substituted $C_1-C_6$ alkyl, optionally substituted $C_1-C_6$ alkenyl, hydroxyl, $C_1-C_6$ alkoxyl, carboxyl, amino or substituted amino, or $Z^2$ is amino or substituted amino and each of $Z^1$, $Z^3$ and $Z^4$ is H, optionally substituted $C_1-C_6$ alkyl, optionally substituted $C_1-C_6$ alkenyl, hydroxyl, $C_1-C_6$ alkoxyl, carboxyl, amino or substituted amino, or $Z^1$ and $Z^2$ are taken together and are an amino or substituted amino derivative of a benzo group and each of $Z^3$ and $Z^4$ is H, optionally substituted $C_1-C_6$ alkyl, optionally substituted $C_1-C_6$ alkenyl, hydroxyl, $C_1-C_6$ alkoxyl, carboxyl, amino or substituted amino.

9. A kit according to claim 7 wherein the aromatic amine is N,N,N',N'-tetramethylbenzidine, 4-benzyloxyaniline, 3-aminofluoranthrene or 4-methoxyaniline.

10. A kit according to claim 7, wherein the peroxidase is present in an analyte in free or conjugated form and its presence or the amount thereof is deduced from the detection or measurement, respectively, of the chemiluminescence.

* * * * *